(12) United States Patent
Cintron et al.

(10) Patent No.: US 6,218,360 B1
(45) Date of Patent: Apr. 17, 2001

(54) COLLAGEN BASED BIOMATERIALS AND METHODS OF PREPARATION AND USE

(75) Inventors: Charles Cintron, Randolph Center, VT (US); Robert Burrows, Lexington, MA (US)

(73) Assignee: The Schepens Eye Research Institute, Boston, MA (US)

( * ) Notice: Subject to any disclaimer, the term of this patent is extended or adjusted under 35 U.S.C. 154(b) by 0 days.

(21) Appl. No.: 09/436,679

(22) Filed: Nov. 9, 1999

Related U.S. Application Data

(60) Provisional application No. 60/109,242, filed on Nov. 19, 1998.

(51) Int. Cl.$^7$ .............. A61F 2/16; A61K 38/39; C07K 14/78
(52) U.S. Cl. .............. 514/8; 514/21; 530/356; 530/409; 623/5.16; 623/6.61
(58) Field of Search .............. 514/8, 12, 21; 623/4, 5, 6, 5.16, 6.56, 6.57, 6.88, 6.59, 6.6, 6.61, 6.62; 530/350, 356, 403, 409, 410

Primary Examiner—Jeffrey E. Russel
(74) Attorney, Agent, or Firm—Lorusso & Loud (57) ABSTRACT

This invention comprises purified native state Type VI collagen/βig, Type VI-βig collagen gel, including the crosslinked gel, and the use of the gel in fibrosis limited wound healing, and methods of preparation of the collagens.

16 Claims, 7 Drawing Sheets

FIG. 6 cxgelsix epithelium stroma

COLLAGEN BASED BIOMATERIALS AND METHODS OF PREPARATION AND USE

RELATED APPLICATIONS

This application claims priority from Provisional Application Ser. No. 60/109,242 filed Nov. 19, 1998.

STATEMENT OF GOVERNMENT RIGHTS

The U.S. Government has a paid-up license in this invention and the right in limited circumstances to require the patent owner to license others on reasonable terms as provided for by the terms of National Eye Institute Grant No. RO1 EY 01099.

FIELD OF THE INVENTION

This invention comprises purified native state Type VI collagen/βig, Type VI-βig collagen gel, including the crosslinked gel, and the use of said gel to limit fibrosis during wound healing, and methods of preparation of said collagens and gels.

BACKGROUND OF THE INVENTION

Type VI collagen, a ubiquitous filamentous structural protein, is an integral component of the interfibrillar matrix, and represents a significant fraction of the connective tissue collagens. A sequence listing of one form of Type VI collagen is found in *Structure and Function of Collagen Types*, Eds. Richard Mayne and Robert E. Burgeson, (Academic Press, New York City (1987)), the teachings of which are incorporated herein by reference. Glutaraldehyde crosslinked Type IV collagen, used as a synthetic epikeratoplasty in monkey is degraded by endogenous enzymes and fails to support a healthy epithelium. (Thompson K P, Hanna K D, Gipson I K, Gravagna P, Waring III G O, Johnson-Wint B., "Synthetic epikeratoplasty in Rhesus monkeys with human type IV collagen," *Cornea*. 1993;12:35–45).

Type VI collagen is one of the earliest matrix proteins deposited during cell infiltration within a collagen tissue polymer composite used to repair an abdominal wall defect. Type VI collagen is a heterotrimer composed of polypeptides α1(VI), α2(VI), and α3(VI). Each polypeptide contains globular domains at the amino and carboxyl termini separated by a short triple-helical domain. The dumbbell-shaped monomers assemble into tetramers by lateral association. End-to-end association of these tetramers forms a beaded filamentous structure.

Type VI collagen is arranged as a beaded filament with about 100 nm periods between beads. Type VI collagen is involved in cell-matrix interactions, and believed to interact with extracellular matrix components including collagens, hyaluronan, and proteoglycans. Without being bound by any particular theory, it is believed that as a structural protein, Type VI collagen plays a role in anchoring basal-lamina-containing organs within connective tissues and restricting lateral movement of collagen fibrils.

Native Type VI collagen co-purifies with a protein identified as βig-h3, a protein induced in a human adenocarcinoma cell line after treatment with TGF-β. This protein in rabbit is termed βig, and is synthesized in corneal stroma during morphogenesis of normal and healing tissue, indicating that it plays a role in these processes. The 683 amino acids sequence of βig has similarity with the protein fasciclin I, a possible surface recognition molecule involved in nerve growth cone guidance, and OSF-2, a protein that has been suggested to function as an adhesion molecule in bone formation.

In corneal stroma, βig is associated with the globular domain of native Type VI collagen. This association involves disulfide-dependent linkages. A denatured Type VI collagen preparation containing βig was reported as promoting adhesion and spreading of corneal fibroblasts and smooth muscle cells in vitro. Adhesion of cells to Type VI collagen and subsequent cell spreading may be partially mediated by βig. As an integral component of the stromal interfibrillar matrix during morphogenesis, βig plays a role in development of an ordered fibrillar matrix. Without being bound by any specific theory, it is believed that such order is necessary for corneal transparency.

We have now, surprisingly, established that corneal Type VI collagen/βig is efficiently extracted without denaturation by means of phosphate buffered saline. The purified preparation, containing Type VI collagen associated with βig forms a viscous substance, which, when concentrated, is in the form of a gel termed "gelsix." We have further discovered that upon chemical crosslinking with polyethylene glycol the gel becomes a transparent film or shaped object. The crosslinked gel is termed "cxgelsix." Cxgelsix is mechanically strong enough to present a useful biomaterial in corneal and other applications.

Numerous studies and patents have described the use of collagens alone or in combination with other components as a biomaterial. Note is made of Thompson K P, Hanna K D, Gipson I K, Gravagna P, Waring III G O, Johnson-Wint B., "Synthetic epikeratoplasty in Rhesus monkeys with human type IV collagen," *Cornea*. 1993;12:35–45; Desgrange P, Tardieu M. Loisance D, Barritault D., "Extracellular matrix covered biomaterials for human endothelial cell growth," *Int J Artif Organs*. 1992;15:722–726; Orgill D P, Ehret F W, Regan J F, Glowacki J, Mulliken J B. "Polyethylene glycol/microfibrillar collagen composite as a new resorbable hemostatic bone wax." *J Biomed Mater Res*. 1998;39:358–363; van Luyn M J A, Khouw M S L, van Wachem P B, Blaauw I H, Werkmeister J A., "Modulation of the tissue reaction to biomaterials. II. The function of T cells in the inflammatory reaction to crosslinked collagen implanted in T-cell-deficient rats," *J Biomed Mater Res*. 1998;39:398–406; van Wachem P B, van Luyn M J A, Damink L O, Dijkstra P J, Feijen J, Neiuwenhuis P., "Biocompatibility and tissue regenerating capacity of crosslinked dermal sheep collagens," *J Biomed Mater Res*. 1994;28:353–363; Werkmeister J A, Edwards G A, Casagranda F, White J F, Ranshaw J A M., "Evaluation of a collagen-based biosynthetic material for the repair of abdominal wall defects," *J Biomed Mater Res*. 1998;39:429–436: Chiou A G -Y, Mermoud A, Underdahl J P, Schnyder C C., "An ultrasound biomicroscopic study of eyes after deep scierectomy with collagen implant." *Ophthalmology*. 1998;105:746–750; and Fujioka K, Maeda M, Hojo T, Sano A., "Protein release from collagen matrices," Advanced Drug Delivery Reviews. 1998;31 :247–266 the teachings of which are incorporated herein by reference. Also noted are U.S. Pat. No. 5,162,430; U.S. Pat. No. 5,219,895; U.S. Pat. No. 5,354,336, the teachings of which are incorporated herein by reference.

SUMMARY OF THE INVENTION

Type Vi collagen, by virtue of its distribution in corneal stroma, its synthesis during morphogenesis, and its interaction with both corneal stromal cells and extracellular matrix proteins, plays an important role in assembling and maintaining proper collagen fibril spacing so necessary for corneal transparency. As an integral component of the stromal interfibrillar matrix during morphogenesis, βig plays a role in development of an ordered fibrillar matrix. Without being bound by any specific theory, it is believed that such order is necessary for corneal transparency.

This invention comprises a purified preparation of Type VI collagen/βig in native state configuration. The invention further comprises a method of preparing purified Type VI collagen/βig in native state configuration comprising the step extracting particularized corneal stroma with substantially isotonic saline in the absence of denaturing extractants. A useful non-denaturing extractant is phosphate buffered saline, optionally in association with a protease inhibitory amount of protease inhibitor.

The invention further comprises Type VI collagen/βig gel. In one embodiment the gel is prepared from Type VI collagen/βig comprising Type VI collagen in native state configuration, and in another embodiment the gel is prepared from collagen comprising denatured Type VI collagen/βig.

The invention yet further comprises a method of preparing Type VI collagen/βig gel comprising the steps of (a) preparing a solution of the purified Type VI collagen;

(b) centrifuging said solution on a centrifugation concentrator filter until a meniscus of Type VI collagen/βig gel is formed on said filter.

Particular note is made of Type VI collagen/βig gel in the form of a crosslinked gel termed "cxgelsix." In one embodiment cxgelsix is prepared by the step of exposing gelsix to a crosslinking effective amount of crosslinking agent. Cxgelsix is understood to be formed either from native state Type VI collagen/βig or to from denatured Type VI/βig collagen or combinations of the two with or without additional ingredients. In one embodiment of this method, the crosslinking agent is disuccinimidyl glutarate polyethyleneglycol, and optionally wherein the crosslinking effective amount is at least about 10:1 crosslinking agent to gelsix (w/w). The product of this process in particularly contemplated within this invention.

The invention is further drawn to a method of potentiating fibrosis limited tissue regeneration by applying cxgelsix to a site of tissue regeneration. In one embodiment, the method is performed wherein the site of tissue regeneration is an incised wound, by the step of applying cxgelsix as a filling for said wound or applying gelsix and converting it to cxgelsix by crosslinking in situ. Note is made that in ophthalmic wounds within the light path for vision, fibrosis limited tissue regeneration is one of maintained substantial transparency. In dermal wounds, fibrosis limited tissue regeneration is associated with minimized on the absence of scarring. In some embodiments the method particularly comprises the steps of (a) applying cxgelsix as gelsix placed in said wound and thereafter (b) contacting said gelsix with a crosslinking agent, and (c) crosslinking gelsix into cxgelsix in situ.

A huge variety of objects useful is post-surgical and implant related procedures are made from cxgelsix. Objects formed from cxgelsix include an intrastromal lens, and a sheet suitable for covering and/or filling a wound.

In a specific embodiment the invention is a fibrosis limiting wound healing kit comprising (a) an applicator containing gelsix (b) an aliquot of excess (relative to gelsix) crosslinking agent, and (c) instructional literature on the in situ intra-wound creation of cxgelsix.

DETAILED DESCRIPTION OF THE INVENTION

This invention will be better understood with reference to the following definitions:

A. "Type VI collagen" shall mean the tetramer composed of the heterotrimer of polypeptides α1(VI), α2(VI) and α3(VI) as described in *Structure and Function of Collagen Types*, Eds. Richard Mayne and Robert E. Burgeson, (Academic Press, New York City (1987)). The heterotrimer is characterized by linear regions of about 100 to about 105 nm ending in globular portions.

Figure 2A:
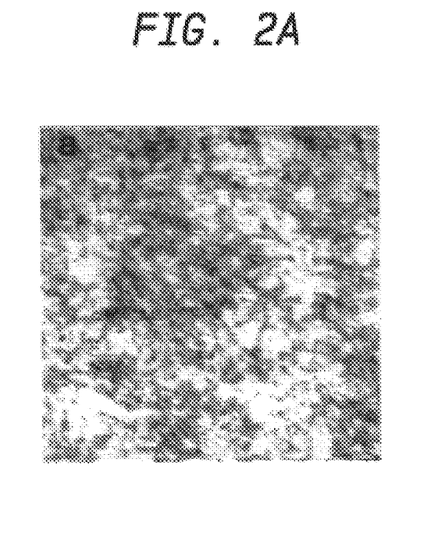
FIG. 2a is an electron micrograph of purified PBS-extracted type VI collagen/βig preparation concentrated on an Amicon filter as gelsix.
Figure 2B:
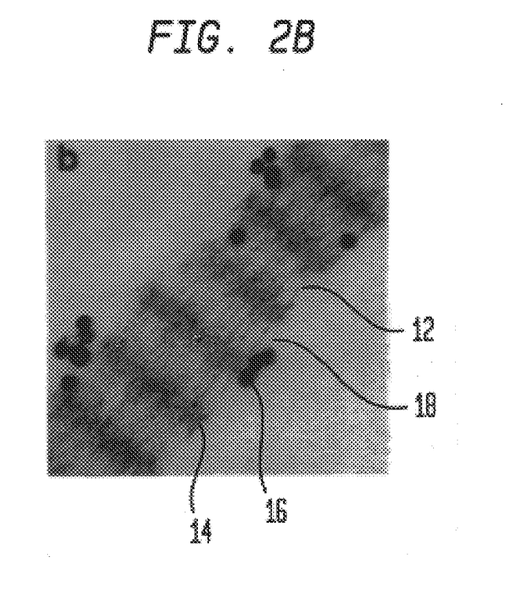
FIG. 2b is an electron micrograph of purified PBS-extracted type VI collagen/βig preparation upon incubation of the gelsix mat of FIG. 2a with acid ATP.

B. "Native state configuration" in reference to Type VI collagen/βig shall mean that the collagen retains the ability to form bundles of Type VI collagen tetramers, 100 nm periodic fibrils ("crystallites") in the presence of ATP as shown in FIG. 2. Note that proteins are termed purified by negative testing—no contaminants found under test conditions. Type VI collagen/βig will be understood to be "purified" Type VI collagen/βig when it presents as substantially a single peak eluted on S-1000 gel at 280 nm near the void volume. Alternatively, purity of Type VI collagen/βig fractions was assessed by sodium dodecyl sulfate polyacrylamide gel electrophoresis (SDS-PAGE). Purified Type VI collagen/βig was chromatographed on Sephacryl S-1000, eluted with SDS/borate buffer, and the eluate assayed for Type VI collagen/βig by SDS-PAGE.

Native state Type VI collagen/βig is prepared in absence of denaturing extractants. By way of example, denatured Type VI collagen/βig was extracted from rabbit corneas with 6 M urea in the presence of iodoacetamide or N-ethylmaleimide. The urea extract was precipitated with ammonium sulfate, redissolved in sodium borate buffer, dialyzed, centrifuged, and chromatographed on a Sepharose CL-4B column. Upon re-suspension the collagen partially renatures as demonstrated by ultracentrifugation analysis.

Urea based extractions denature Type VI collagen but do not separate βig which is covalently linked by sulfhydryl linkages. These can be broken by such reagents as beta mercapto ethanol and dithiothreitol (DTT).

C. "Particularized" as related to corneal stroma as a raw material for extraction shall mean the small particulates, generally less than about 1 mm. Particularization yields high surface area, the result of corneas that are frozen and pulverized in a mill type preparation (e.g., a Wiley mill). In particular embodiments, particulates are powdered or made into small particles by any of a number of methods known to those skilled in the art as a suitable pre-extraction but non-denaturing step for biomaterials.

D. "Salt" relevant to solutions for the extraction of Type VI collagen/βig in native state configuration shall mean sodium, potassium or calcium, with particular TO reference to phosphate buffered saline, and specifically isotonic phosphate buffered saline.

E. "Protease inhibitory amount" of "protease inhibitor" shall mean an amount sufficient to deactivate the proteases present in a collagen containing aliquot being purified. Protease inhibitors known in the art include, Antipain, Na-t-BOC deacetylleupeptin, propionyl-leupeptin, and pepstatin A.

C. "βig" shall refer to the protein as disclosed in Rawe IM, Zhan Q, Burrows R, Bennett K, Cintron C., "βig: Molecular cloning and in situ hybridization in corneal tissues," *Invest Ophthalmol Vis Sci.* 1997;38:893–900. βig is synthesized during morphogenesis of normal and healing corneal stroma. This is similar to a protein induced in a human adenocarcinoma cell line after treatment with TGF-α. The 683 amino acids sequence (Id.) of βig has some similarity with an insect protein fasciclin I, a possible surface recognition molecule involved in nerve growth cone guidance, and OSF-2, a protein that has been suggested to function as an adhesion molecule in bone formation. βig is also termed βig-h3, keratoepithelin, MP78/70, RGDCAP/βig-h3 and P68βig-h3.

D. Gel shall mean the viscous state in which most collagen is found in vivo. Gelsix is a transparent gel of Type VI collagen in association with βig. In some instances the Type VI component of gelsix is a denatured Type VI collagen, and in some instances it is in native state configuration or combinations of native state configuration and denatured states. Gelsix is a gel that can be mounded up several millimeters on a filter paper. It exhibits elasticity and retains some shape but cannot be picked up with a tweezers in a bolus. The gel is viscoelastic, and as such exists as a gel solution, a fluid which resists flow by nature of high viscosity. These fluids are elastic because they have a "memory." They return to approximately their original shape after stretch. In many instances, these solutions are optically clear and are basically aqueous solutions of higher molecular weight polymers in the molecular weight range of from at least about 2,000,000 Daltons.

E. "Crosslinking agent" shall mean any of a wide variety of agents to cross link proteins. These include vegetable tanning materials, aromatic carbohydrate derivatives of phenols, metal salts, aldehydes, diisocyanates, sulfochlorides, diglycylethers, epoxides, quinones, and carbodiimides as well as UV light and radiation. Particular note is made of succinimidyl glutarate polyethyleneglycol, a pharmaceutically acceptable crosslinking agent.

F. Cxgelsix is crosslinked Type VI collagen and βig. In cxgelsix, "crosslinking" shall mean collagen molecules linked by covalent bonds to polyfunctional (including difunctional) polymers. Cxgelsix is inclusive of crosslinked gel derived from gelsix with its origin in native state Type VI collagen, but also from denatured Type VI collagen and combinations of native state and denatured. In general, crosslinking is accomplished in a substantial excess of crosslinking agent. For example 1.5 mg of gelsix exposed to a 50 mg/ml solution of succinimidyl glutarate polyethyleneglycol at 30:1 crosslinking agent to gel is such a substantial excess. Crosslinking is complete in a matter of about one to several minutes. Cxgelsix is firm and rubbery and is firm enough to be held in place by sutures. Cxgelsix is also characterized by sufficient $CO_2$ and $O_2$ transport to maintain ophthalmic tissues covered by preparations several $\mu$m thickness. It is a particular advantage of cxgelsix, that in situ, such as when embedded intrastromally, it does not display a clinically adverse affect on surrounding, here, corneal tissues, and remains intact in the presence of an acute inflammatory reaction during (corneal) wound healing.

It is to be particularly understood that Type VI collagen (native state and denatured) also forms a gel in the absence of βig which is usefully crosslinked.

It is further understood that for some applications and uses cxgelsix is dehydrated or dried as by mild heating or by lyophilization, and thereafter rehydrated at the time of use. For such applications, thin structures such as wound cover type sheets of about 1 to 3 mm in thickness are preferred for the ease of rehydration. Rehydrated structures used as sterile mechanical barriers are noted.

G. "Fibrosis limiting" or "limited" shall mean that upon infiltration and replacement cxgelsix by replacement tissue, less than about 50% of the infiltrating tissue will be scar tissue, and in some embodiments less than about 30% and in some embodiments, less than about 10%. In ophthalmic applications within the visual path, fibrosis limiting will mean highly translucent to substantially transparent permitting shape determination, and in particular embodiments, normal or near normal vision.

H. "Replacement tissue" shall mean tissue of similar function to the site or replacement, and replacing damaged or excised tissue, such as is found in the healing process following wound or trauma.

I. "Stability" as to the in vivo integrity of cxgelsix ("in vivo-stable") was established during exposure to endogenous enzymes with particular reference to those encountered with inflammation and wound healing. In fact, it is only after many months that even partial degradation of a cxgelsix implant occurred. In these instances the cxgelsix implant was replaced over a period of months with bundles of fine collagen fibrils reminiscent of normal cornea.

The use of the gels described herein is to be broadly understood. Contemplated uses include augmentation, repair, prevention, or alleviation of spatial defects such as those due to loss or absence of soft tissue or soft tissue support, or to the lose or absence of hard tissue, i.e., bone. In particular embodiments therapeutic uses included using therapeutic agents impregnated into or coupled with the claimed gels of this invention. Exemplary agents are anti-inflammatory, anti-infective, and immunomodulatory agents. Restoration/establishing of normal (or desired) dermal or optic contours are notable uses of cxgelsix. In some instances the gel will be malleable upon placement in situ (even if crosslinking is initiated or continues post-placement), and in others it will comprise a solid shape or implant when placed. Implants as disclosed in U.S. Pat. No. 5,162,430 to Rhee et al. are noted, the teachings of which are incorporated herein by reference.

EXAMPLE 1

Cxgelsix in vivo Properties

An intralamellar 4.0-mm-diameter disc of Cxgelsix was implanted in the corneal stroma. The implant did not alter the structure of corneal epithelium above the implant. This is evidence of normal or near-normal transport of nutrients through in situ cxgelsix. Moreover, no structural abnormalities were seen in the rest of the cornea and the cornea remained transparent. After implantation, the cornea accepted the presence of cxgelsix disc as judged by clinical criteria including the absence of clinically observed inflammatory response. Gradually and over a period of months degradation of the implant was observed by ultrastructural observation.

EXAMPLE 2

Type VI collagen/βig-Purification

Type VI collagen/βig from the rabbit cornea was extracted, purified, and prepared as a gel by a non-denaturing method. Details of the extraction and purification of Type VI collagen/βig are as follows:

Corneal stromas obtained from rabbit corneas (PelFreez, Rogers, Ark.) were frozen and pulverized in a Wiley mill. Powdered corneal stroma was extracted several times with phosphate buffered saline (PBS), pH 7.0 containing a protease inhibitor cocktail. The extracts were pooled, filtered, and concentrated on an Amicon diafiltration with a YM10 filter (Amicon Inc. Beverly, Mass.). The concentrate was centrifuged, and the pellet discarded. The supernatant was then put through a CL2B (Sigma, St. Louis, Mo.) column, and eluted with PBS containing 0.02% sodium azide. The eluate was monitored spectrophotometrically at 280 nm, and Type VI collagen/βig eluted near the void volume followed by a broad peak of lower-molecular-weight material. Fractions containing Type VI collagen/βig were pooled, concentrated, and recycled through the gel filtration column two additional times. The PBS extract was concentrated by ultrafiltration, and chromatographed on a CL-2B column. Purity of Type VI collagen/βig fractions were assessed by sodium dodecyl sulfate polyacrylamide gel electrophoresis (SDS-PAGE). Purified type VI collagen was chromatographed on Sephacryl S-1000, eluted with SDS/borate buffer, and the eluate assayed for type VI collagen and βig by SDS-PAGE. Mono-specific rabbit polyclonal antibodies to βig were used for immunocytochemical analyses of human fetal corneas. Adenosine triphosphateinduced crystallite formation and immunogold analysis of the Type VI collagen/βig preparation was used to confirm identification of the purified PBS extract. Immunochemical analysis of the purified type VI collagen preparation was conducted by rotary shadowing.

Figure 1A:
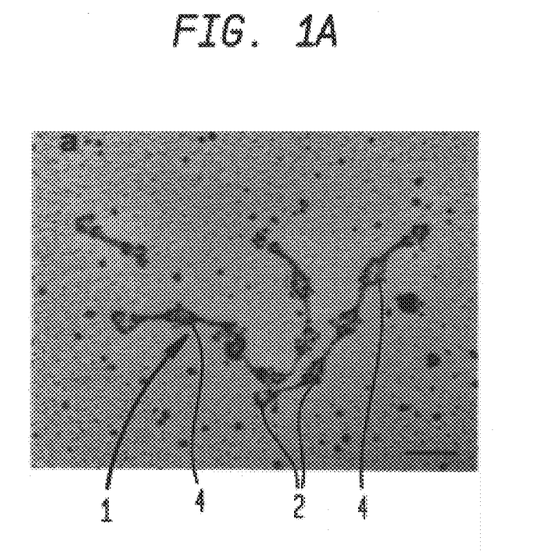
FIG. 1a is a rotary shadowing electron micrograph of purified PBS-extracted type VI collagen preparation.

FIG. 1a is a rotary shadowing electron micrograph of purified PBS-extracted type VI collagen preparation. The sample was incubated with non-immune serum shows the characteristic beaded filaments. The filaments of Type VI collagen (1) are composed of discrete dumbbell-like units associated end to end (2). Small unknown spherical structures associated with the globular domains (4) of type VI collagen are evident (4). Bars=100 nm.

Figure 1B:
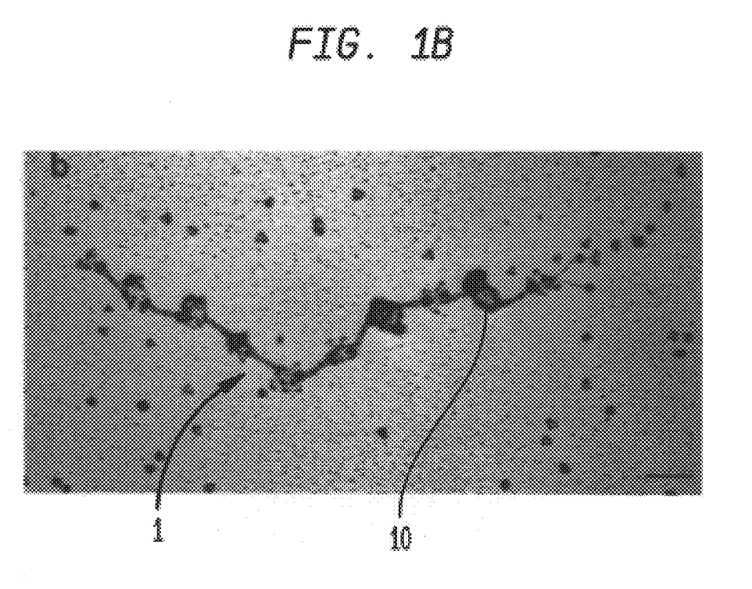
FIG. 1b is a rotary shadowing electron micrograph of purified PBS-extracted type VI collagen preparation mixted with antibodies specific to βig.

FIG. 1b is a rotary shadowing electron micrograph of purified PBS-extracted Type VI collagen preparation. Type VI collagen preparation was incubated with antibody against βig (anti-βig). It shows filaments of Type VI collagen (1). Irregularly enlarged globular structures (10) are the association of anti-βig with some of the globular domains of Type VI collagen. Bars=100 nm.

FIG. 2a is an electron micrograph of purified PBS-extracted Type VI collagen/βig preparation concentrated on an Amicon filter as gelsix. Type VI collagen appears as an aggregate of a mat of filaments uniformly distributed. Bar=100 nm.

FIG. 2b is an electron micrograph of purified PBS-extracted Type VI collagen/βig preparation upon incubation of the gelsix mat of FIG. 2a with acid ATP. The filaments (12) of Type VI collagen in native state configuration are converted to a highly organized ladder-like structure (18) characteristic of Type VI collagen. Immuno-gold labeling (16) of the ladder-like structure with antibody specific to Type VI collagen at the globular domain (14) indicates this structure is composed of Type VI collagen. Bar=100 nm.

Figure 3:
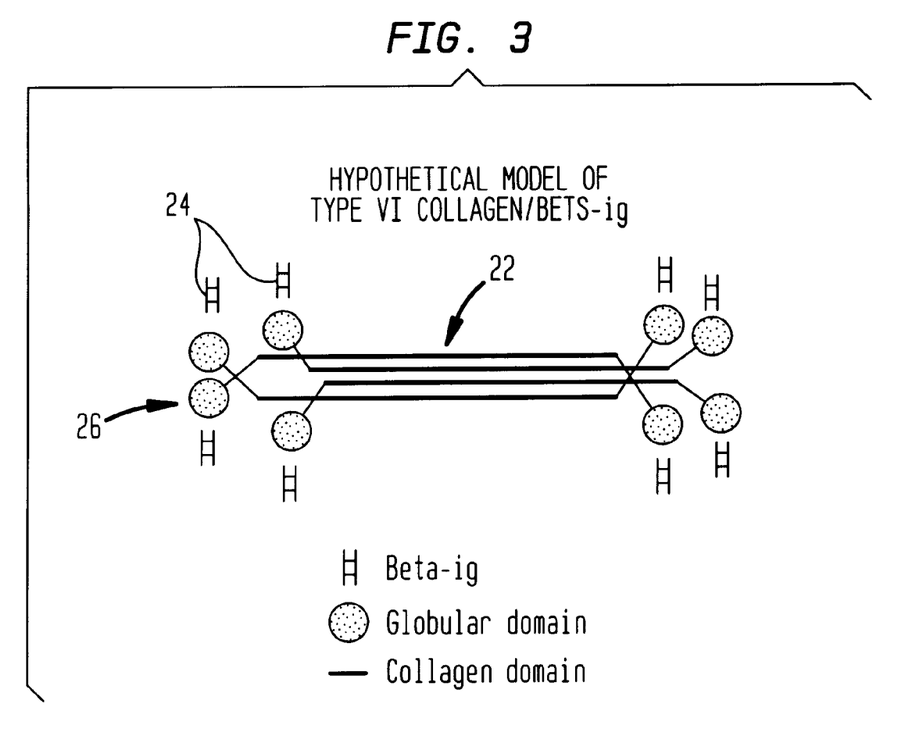
FIG. 3 is a hypothetical model of type VI collagen/βig. The stoichiometry of βig to Type VI collagen is believed variable.

FIG. 3 is a hypothetical model of type VI collagen/βig. The stoichiometry of βig to Type VI collagen is believed variable. A tetrad of Type VI collagen fibrils (22) are arranged in parallel as shown. The βig (24) is associated with the globular domains (26) of the Type VI collagen alpha polypeptides. Although the figure shows one molecule of βig-associated with each globular domain, the stoichiometry varies in specific instances.

EXAMPLE 3

Gelsix Preparation

Approximately 0.15 mg of purified Type VI collagen/pig was placed in a Centricon concentrator (Amicon, Beverly, Mass.) and centrifuged in a swinging bucket at 5000×g for approximately 1 hour, depending on the initial volume of the sample, until a meniscus was formed on the filter of the concentrator. The resulting product was gelsix. FIG. 2a.

EXAMPLE 4

Cxgelsix Preparation

The gelsix of Example 3 was crosslinked on the surface of the filter of Example 3 with 0.1 ml of disuccinimidyl glutarate polyethyleneglycol (di-SG-PEG,MW 3400) (Shearwater Polymers, Inc. Huntsville, Ala.), 50 mg/ml H2O, for 15 minutes before centrifugation for 30 minutes. The crosslinked gelsix was then washed with 0.2 ml PBS three times and centrifuged after each wash. To easily view the implant, cxgelsix was stained with 0.2 ml of 5-([4,6-dichlorotrazin-2 -YL]amino)-fluorescein hydrochloride, (Sigma Chemical Co., St. Louis, Mo.) (DTAF), 5 mg/ml in 0.2 M sodium bicarbonate, a non-toxic fluorescent dye that covalently binds to collagens. Cxgelsix was stained for 15 minutes, excess dye removed, and the gel washed with PBS as above. The Centricon tube was disassembled, and the gel floated off the filter in a bath of PBS.

Discs of cxgelsix, 2.0 and 4.0 mm in diameter, were cut out from the gel with a trephine. Stained cxgelsix, sterilized with sodium azide during isolation and purification of Type VI collagen, was extensively washed in sterile PBS, pH 7.2, and kept in 3 ml of sterile PBS containing 6 drop of 0.3% Ciprofloxacin HCl eyedrop (Alcon Laboratories, Inc, Fort Worth, Tex.) for at least one hour, followed by UV exposure for 15 minutes in a tissue culture hood to ensure sterility prior to implantation in the corneas. The cxgelsix discs implanted in corneas ranged in thickness of from 9 to 35 µm, as determined by electron microscopy. In a separate preparation, the water content of the gel was determined to be approximately 87% by weight.

EXAMPLE 5

Cxgelsix in vivo Placement & Tolerance

Adult rabbits were prepared for this study using procedures in accordance with the Association for Research in Vision and Ophthalmology Statement for the Use of Animals in Ophthalmic and Vision research. To determine the response of corneal tissues to the presence of cxgelsix intrastromally, 10 adult rabbits were anesthetized with intramuscular injection of a Ketamine, Xlyazine, and Ace Promazine, 0.5–0.7 ml/kg body weight, and received topical anesthesia with 0.5% Proparacaine Hydrochloride Ophthalmic Solution (Sight Pharmaceuticals, Inc, Tampa, Fla.) on their corneas. The eyes were proptosed for immobilization and the ocular surface was flushed with a topical antibiotic eye drop (0.3% Ciprofloxacin HCl) before surgery. An 8.0-mm-diameter corneal circle in the left eye was delineated with a trephine. A groove, deepened to approximately 0.2 mm, was made in a small area of the temporal quadrant to form a corneal lip. This tissue was then slightly elevated with Colibri forceps and an interiamellar dissection was started with a Martinez double ended corneal dissector knife (Storz Instrument Co, St Louis, Mo.). The plane was enlarged laterally toward the corneal apex by oscillating horizontal movements. After the temporal two third corneal flap was made, a 4.0-mm-diameter cxgelsix disc was carefully placed on the stromal bed and centered over the pupil. The flap was replaced over the implant without sutures. Surgical placement of all cxgelsix implants were performed by the same surgeon. The right eye of each rabbit served as a sham control to evaluate the effects of free hand lamellar dissection.

The rabbits were divided into two groups. Group A, consisting of five rabbits, were not exposed to steroid prior to or after cxgelsix implantation. In group B, also consisting of five rabbits, the cxgelsix disc was washed with 0.1% Fluorometholone Acetate, FML, (Allergan Medical Optic, Irvine, Calif.) prior to implantation, and both eyes were treated with this topical steroid eye drop during the postoperative period, once a day for seven days. In group A and group B, topical antibiotic (0.3% Ciprofloxacin HCL) was instilled immediately on all corneas after the procedure and in the early post-operative period three times a day for seven days. Three days post-operative Neomycin-Polymyxin B Sulfates-Bacitracin Zinc eye ointment (Akorn, Abita Springs, La.) was given topically once a day for seven days.

Cinical postoperative examinations were performed on the $3^{rd}$ and $7^{th}$, $14^{th}$ and $21^{st}$ days after surgery, and monthly for 4 months. The rabbits were then euthanized with an intravenous overdose of pentabarbital and the corneas were removed to determine the status of the implants and the corneal cells by light arid transmission electron microscopy. The samples were fixed in 2% paraformaldehyde and 2.5% glutaraldehyde in 0.1 M cacodylate buffer, pH 7.4, and dehydrated in a graded ethanol series and embedded in Poly/Bed 812 (Polysciences, Warrington, Pa.) to obtain ultra-thin sections on grids. Grids were stained in 4% uranyl acetate in 50% ethanol for 25 minutes, followed by Reynolds' lead citrate for 5 minutes, and examined with a Philips 410 transmission electron microscope.

Except for three eyes, the corneal epithelia of both groups were clinically normal based on negative staining with Rose Bengal. The experimental eye of one rabbit from group A presented with a minor corneal erosion at day 50, but recovered again at day 60. In group B, the steroid-treated animals, the experimental eyes of two rabbits had mild superficial keratitis only during the first week after surgery. Minimal subepithelial infiltrate in these eyes was present anterior to the implant area, in an otherwise clear cornea. Fifty five percent of all eyes showed corneal flap retraction, 6 eyes in group A (no steroid treatment) and 5 eyes in group B (steroid treatment). Of these, 7 eyes had implants versus 4 sham controls. Three eyes in group A, one with the implant and two in the sham controls developed mild superficial corneal neovascularization that failed to extend beneath the flaps. Two, in group A with implants, developed corneal flap thinning, in the mid-periphery area near the original incision at day 45 and day 50. A summary of the complications for both groups indicate that the steroid had some ameliorating effects on several complications. Throughout the follow up time, the implant remained transparent and survived intact with no sign of infection in any of the eyes. Taken together, the presence of the cxgelsix implant failed to markedly alter the structural integrity of the cornea based on clinical observations. The DTAF stained cxgelsix implant remained clear and intact during the 4 month period of study. No obvious changes in corneal thickness were evident by slit lamp microscopy.

Although the histologic appearance varied from eye to eye, the general pattern of results were consistent. The structure of the cornea 4 months after the sham surgical procedure without post-surgical steroid treatment showed minimal changes. The epithelium was composed of 4–5 layers of cells with a distinct line representing the basement membrane. In some cases the location of the original lamellar dissection was indicated by a slight difference in the staining intensity of the stroma. The stroma and Descemet's membrane posterior to the original incision appeared normal. The contralateral eye, containing the cxgelsix corneal implant for 4 months, showed a homogeneously stained structure located parallel to the surface about one third to one half the depth of the stroma from the surface of the cornea. In some cases the implant contributed to the overall thickness of the cornea. This, however, did not have any effect on the appearance or thickness of the epithelium, stroma, or Descemet's membrane in comparison to the sham control. In all cases examined the cxgelsix implants were associated with numerous cells having rounded nuclei and dark-stained cytoplasmic granules. The number of cells associated with implants varied considerably along their length. Eyes treated with steroid prior to the surgical procedure were histologically indistinguishable from those not treated with steroids. As with the non-steroidal samples, a variable number of cells containing dark-stained granules were seen adjacent to the implant. Again, the epithelium, the stroma above and below the implant, and Descemet's membrane appeared normal. Moreover, the epithelium and stroma failed to show any abnormalities associated with the presence of the implant other than the presence of large granular-containing cells adjacent to the implant.

EXAMPLE 6

Cxgelsix in vivo Placement & Tolerance

Corneal response to cxgelsix was further determined via Transmission Electron Microscocopy. Corneal ultrastructure at four months confirmed clinical and histological observations, showing that the epithelium above the implant was; normal in comparison to the shame control. The epithelial structure in both tissues consisted of basal, wing, and squamous cell layers with no indication of epithelial edema. Furthermore, an intact and uniform basement membrane failed to indicate any previous damage. The stroma above and below the cxgelsix implant contained bundles of collagen fibrils and occasional stromal cells with minimal cell organelles indicative of normal quiescent cells. No stromal differences were seen between steroid and non-steroid-treated corneas. Cxgelsix implants appeared ultrastructurally as dense homogeneous structures having a uniform thickness for each sample. The thickness of the implant, however, varied from one preparation to another ranging from about 9 to about 35 $\mu$m. In some instances, small electron lucent pores were seen within the implant. Along the upper and lower surfaces of the implant the structure of the matrix and cellular profile varied. Some regions showed no discernable alteration of the implant structure or adjacent stromal cells. In other regions, irregularities in the implant surface and pockets containing cellular material within the implant could be seen associated with the presence of macrophages. In some cases, macrophages were numerous, and associated with marked structural alterations in the implant.

EXAMPLE 7

Cxgelsix in vivo Stability

To determine the stability of cxgelsix in the presence of a healing corneal wound, six adult rabbits were anesthetized and prepared for surgery as described above. In each corneal stroma of both eyes a pocket extending 2–3 mm from the limbus and ending near the center of the cornea was made with a Troutman knife (Weck/Xomed-Treace, Jacksonville, Fla.). A 2.0 mm-diameter button of cxgelsix was introduced into each pocket and allowed to heal in place near the center of the cornea. After 1 week of healing, each rabbit was prepared for surgery as before and a 2.0 mm-diameter trephination wound was made in each eye adjacent to the cxgelsix implant (Cintron C, Schneider H, Kublin C. "Corneal scar formation," *Exp Eye Res.* 1973;17:251–259). Each eye received antibiotics each day for three days as described above and watched carefully to make sure no infections developed. The eyes were examined each week by slit lamp microscopy and photographed. At 11 and 30 weeks after wounding, rabbits were killed with an overdose of sodium pentobarbital, the eyes enucleated and immediately fixed and processed as above in preparation for transmission electron microscopy.

Formation of a stromal pocket to accommodate a 2.0 mm disc of cxgelsix was intentionally crudely done to stimulate inflammation. Edema, associated with the formation of the stromal pocket was noted one day after surgery. Nevertheless, all eyes, except for one, accepted the implant without vascularization. The animal with a vascularized cornea was eliminated from the study. A 2.0 mm diameter excision wound was then made adjacent to the cxgelsix one week after implantation and allowed to heal. After 1 week of healing, all eyes were clinically progressing well. In all instances a white, avascular scar tissue was deposited along the edge of the wound leaving the center occupied by a fibrin clot. The wound was subsequently filled completely by avascular scar tissue by the second to third post-operative week. One week after the excision wound was made two eyes showed neovascularization at the limbus extending toward the implant. By the third week after implantation, 2 weeks after wounding, the vascularization subsided in the two eyes and subsequently regressed. No apparent changes could be seen in the implants during the first 3 weeks after wounding. On week 8 small brown deposits were seen along the edge of the implants. These deposits progressively became larger by week 16. In some instances, cxgelsix associated brown deposits were noticeably decreased by week 30. The results indicate that some degradation of the implant occurs during the initial stages of wound healing. The implant, however, persisted for over 7 months without further degradation.

EXAMPLE 8

Cxgelsix in vivo Stability Transmission Electron Microscopy

Figure 7A:
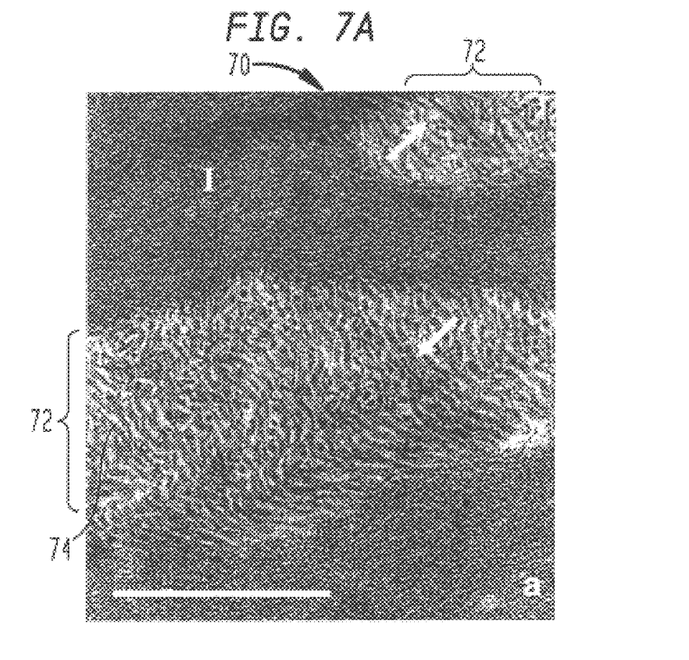
FIG. 7a is an electron micrograph of a cxgelsix corneal implant at 30 weeks.
Figure 7B:
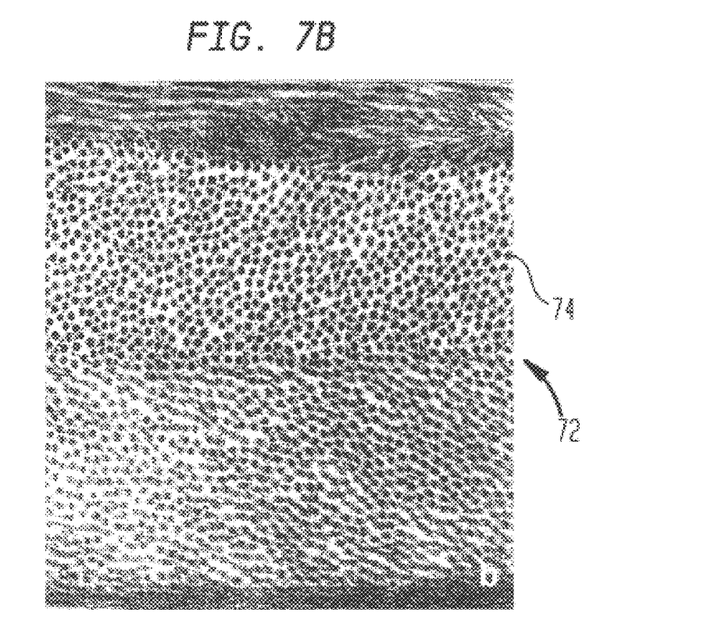
FIG. 7b is a detailed electron micrograph of normal corneal stroma in cross section.

After cxgelsix implants, corneal epithelium and subjacent stroma appeared normal over the cxgelsix implant 11 weeks after wounding. Deeper in the cornea, however, numerous cells were congregated around the implant. Based on their morphological appearance, most of the cells were identified as macrophages and fibroblasts. A fine granular-filamentous electron dense material, presumably fibrin, was interspersed between the stroma and cellular infiltrate. By 30 weeks, most of the cells associated with the implant were fibroblastic with few macrophages. The fibroblasts were characterized by the abundance of rough endoplasmic reticulum and elongated nuclei. An implant (70) is shown as the dark area of FIG. 7a marked "I." Spaces noted within the implant (70) were termed "lacunae" (72) which are marked with arrows. Lacunae were filled with fine collagen fibrils (74) as shown in FIG. 7a. Along the surface of the implant the extracellular matrix contained small bundles of collagen fibrils separated by electron dense material reminiscent of lamina densa and similar to the normal but larger lamellae of the cornea and indicating transparency. FIG. 7b, the normal corneal stroma (72) were found to be composed of fine collagen fibrils (74) as seen in cross section, having diameters similar to those found in FIG. 7a. Thus the FIG. 7a corneal fibrils are organized rather differently than the normal condition but with order and spacing confirming substantial light transmission. The variability in fibril orientation distinguished them from normal. Taken together, it appeared that the early stages post-implant, are characterized by the invasion of the implant primarily by inflammatory cells, followed by fibroblasts and associated collagen fibrils that infiltrate and encapsulate the implant.

The results of the studies disclosed below show clearly that implants of cxgelsix were remarkably, even as challenged by endogenous enzymes during post-implantation inflammation and wound healing. Cxgelsix is degraded over time—on the order of at least about 6 or more months—by inflammatory and fibroblastic cells, and replaced by bundles of collagen fibrils having diameters similar to that seen in normal cornea. Although the organization of the fibrils, within the lacunae of the implants, were not rigidly parallel to each other, the tight packing of the bundles were similar to that in normal cornea, suggesting that the fibril-filled lacunae were transparent. While again not being bound by any theory, it is believed that the gradual replacement of cxgelsix by collagen fibrils synthesized by stromal fibroblasts results in the formation of a transparent tissue similar to normal stroma. This is possible because the deposition of matrix associated with the implant occurs in the absence of polymorphonuclear leukocytes, characteristic of the early periods of healing. In our model, the trephination wound heals rapidly with the deposition of an opaque scar tissue by 2–3 weeks, but the cxgelsix implant adjacent to the scar remains transparent initially, and also upon its gradual infiltration and replacement with new transparent matrix. The deposition of matrix around and within the cxgelsix adjacent to the wound occurs late, perhaps after 11 weeks, well after the acute inflammatory reaction in the trephination wound has subsided. At this time the corneal epithelium and surrounding stroma has returned to its normal structure, effectively sealing the implant from further interaction with tear-borne inflammatory factors and polymorphonuclear leukocytes, present only during early periods of healing. The de novo deposition of implant-associated matrix occurred in the absence of polymorphonuclear leukocytes. As in fetal wound healing, the new matrix was deposited without the formation of scar tissue.

Isolation and preparation of cxgelsix from rabbit corneal stroma in this study was accomplished under non-denaturing methods.

It is stressed that the results of these experiments support the invention in establishing that cxgelsix implants were accepted by corneal tissues based on clinical and morphological criteria. Moreover, the normal appearance of the epithelium above the implant indicated that nutrients are able to pass through the implant to maintain the epithelium. A sheet of cxgelsix on cornea denuded of epithelium, will serve as a substrate for the regenerating epithelium and allow establishment of a normal anchoring structure, including lamina densa and anchoring fibrils. No marked histologic or ultrastructural differences in the integrity of the cxgelsix implant were seen between steroid-treated and untreated eyes.

The apparent resistance of cxgelsix to degradation by endogenous enzymes is useful for anchorage of prosthetic devices to living tissues, such as corneal prostheses. By virtue of its role as a substrate for fibroblasts, and resistance to rapid degradation, chemical crosslinking of gelsix in vivo is usefully employed in a method of in situ formation of biological glue for healing wounds. In particular embodiments, crosslinks are further formed between Type VI collagen and collagens at the cut edge of the wound, as well as between Type VI filaments.

EXAMPLE 11

Use of Cxgelsix

Figure 4A:
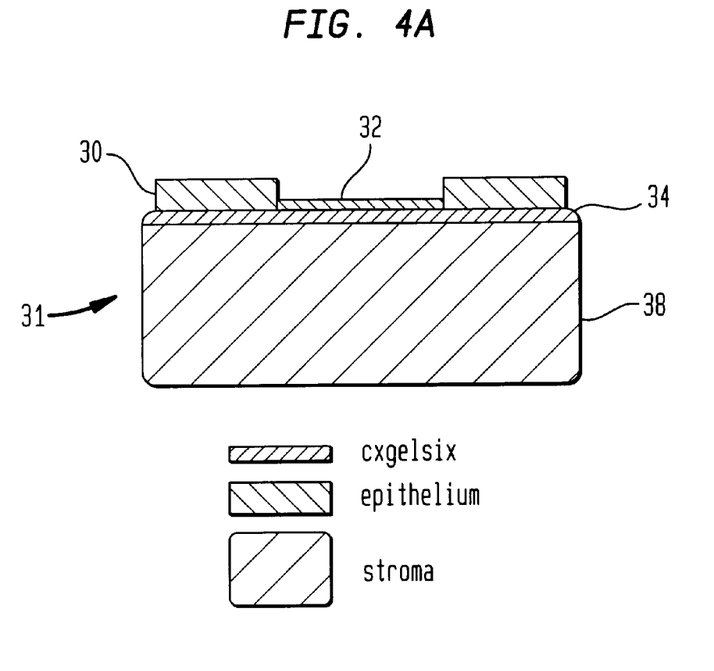
FIG. 4a is a diagrammatic view of a cornea with an epikeratoplastic wound dressing sheet of cxgelsix at the time of initial dressing.
Figure 4B:
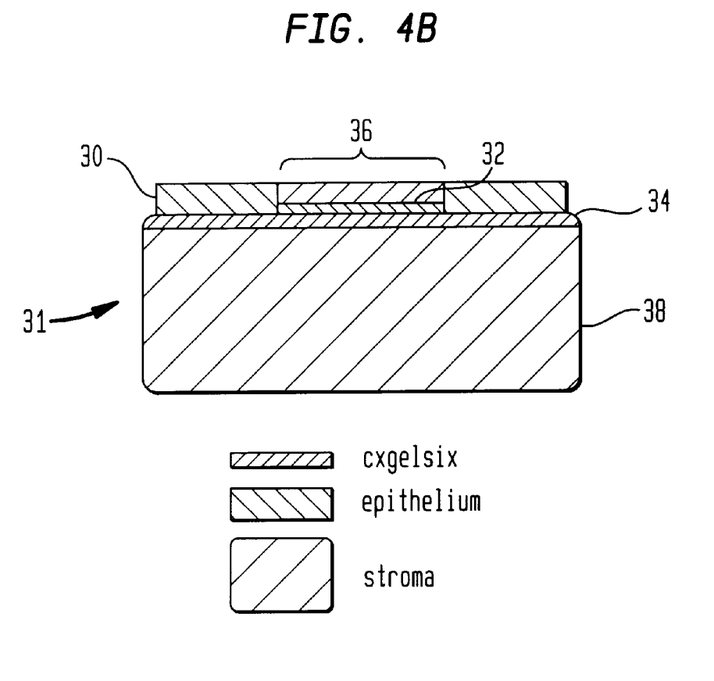
FIG. 4b is a diagrammatic view of a cornea with an epikeratoplastic wound dressing sheet of cxgelsix at about one to two days post-injury.
Figure 5A:
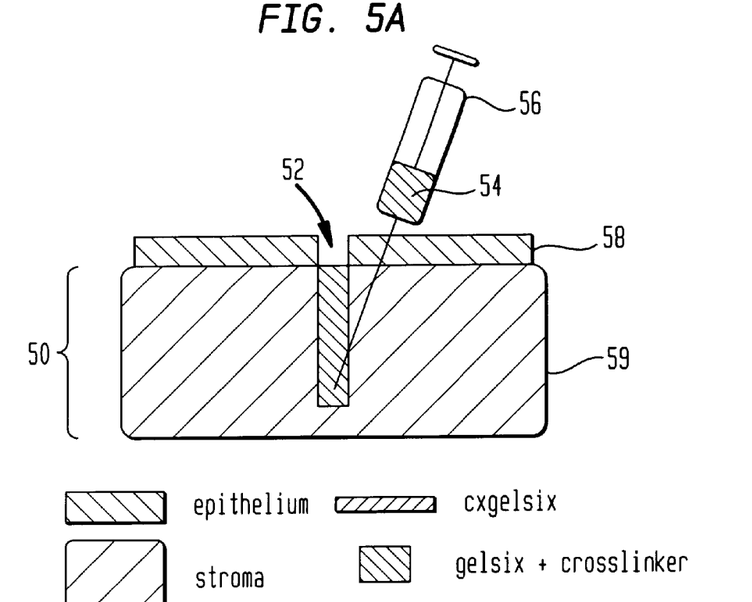
FIG. 5a is a diagrammatic view of a cornea after radial keratectomy/dermal incision undergoing injection with gelsix and crosslinker to form cxgelsix plug.
Figure 5B:
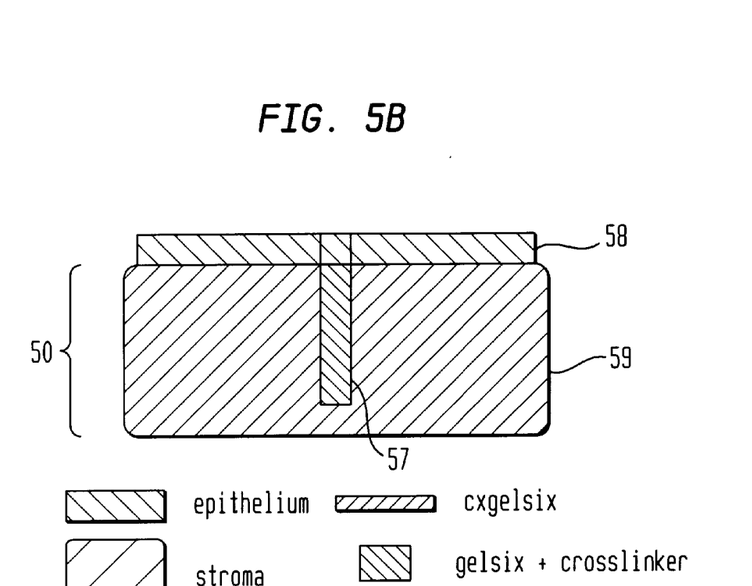
FIG. 5b is a diagrammatic view of a cornea healing from radial keratectomy/dermal incision and use of a cxgelsix plug.
Figure 6:
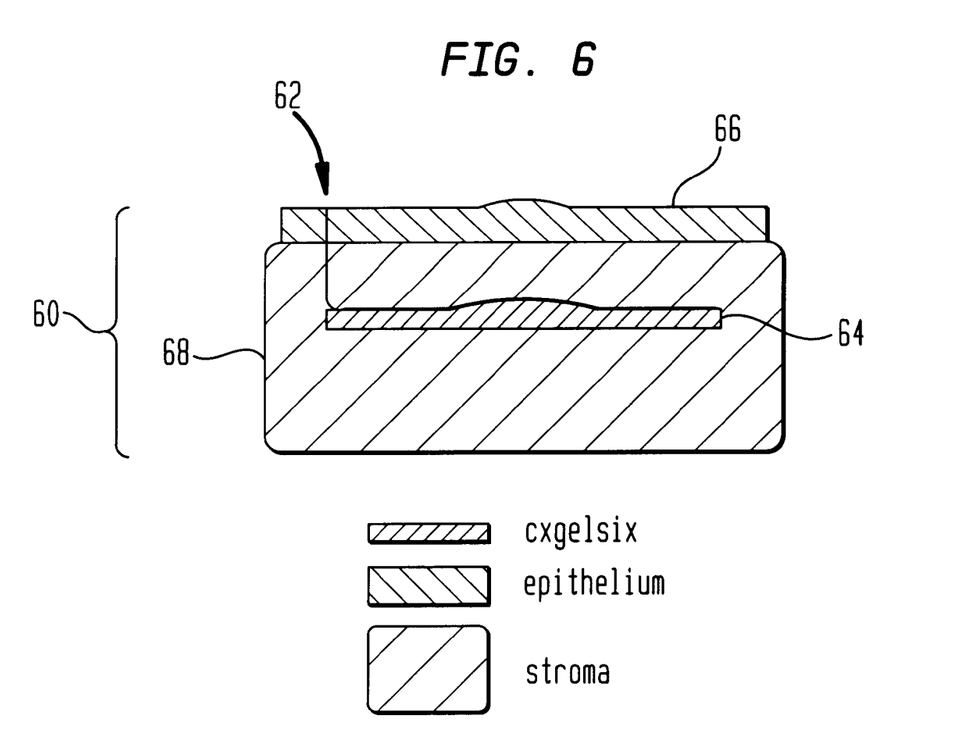
FIG. 6 is a diagrammatic representation of cxgelsix as an intrastromal lens.

As to uses of cxgelsix, attention is drawn to FIGS. 4 through 6. FIG. 4a is a diagrammatic view of a cornea (31) with an epikeratoplastic wound dressing sheet of cxgelsix at the time of initial dressing.

FIG. 4b is a diagrammatic view of a cornea (31) with an epikeratoplastic wound dressing sheet of cxgelsix at about one to two days post-injury.

The corneal epithelium is (30). Damaged corneal epithelium is removed from the central cornea and a sheet of cxgelsix (32) is sutured or glued on to the basement membrane or Bowman's membrane (34) demarking the cornea from the substantia propria or stroma (38). Within a few days, the limbal epithelium (36) grows over the cxgelsix sheet, and attaches itself to the sheet by synthesizing anchoring structures.

FIG. 5a is a diagrammatic view of a cornea undergoing radial keratectomy/dermal incision cxgelsix plug. FIG. 5a is a diagrammatic view of a cornea (50) undergoing radial keratectomy/dermal incision cxgelsix plug. An incision (52) in corneal or dermal tissue is filled with a mixture of gelsix and crosslinker (54) from an applicator, here syringe (56). One useful crosslinker is polyethylene glycol. The gelsix and crosslinker is introduced into the incision running from the corneal endothelium (58) into the stroma (59). In FIG. 5b the gelsix is cxgelsix (57) and the endothelium (58) has grown over the wound.

FIG. 5b is a diagrammatic view of a cornea healing from radial keratectomy/dermal incision and use of a cxgelsix plug.

The proportion of crosslinker to gelsix will determine the rate of polymerization to turn the mixture into cxgelsix. Subsequent healing by the epithelium traps the plug of cxgelsix within the tissue. The cxgelsix is eventually replaced by normal extracellular matrix by adjacent fibroblasts.

FIG. 6 is a diagrammatic representation of cxgelsix as an intrastromal lens;. Cxgelsix can be molded in the form of a lens as shown in FIG. 6. A cornea is shown on cross section (60). To implant such lens, a lamellar dissection through the corneal epithelium (66) is made in the cornea (60) to form a flap of tissue in the corneal stroma (68). The incision is marked as line (62). The cxgelsix lens (64) is placed on the exposed surface of the stroma and the flap is replaced with or without a stabilizing suture. The thickness and shape of the lens will alter the curvature of the anterior stroma, changing the refractive properties of the cornea.

As an element of a radial keratotomy procedure to correct myopia, a cornea is incised by a keratotomy knife radially from the lens. The incision is 1 mm deep and 3 mm in length. The wound is covered by a sheet of cxgelsix 5 mm×5 mm and having a 1 mm v shaped protrusion that inserts into the incision. (FIG. 5) The sheet is glued at the edges. In the ensuing 5 days, healing in the cornea causes new transparent tissue to infiltrate the gelsix within the wound thus leaving a transparent and reshaped cornea.

The compositions of this invention possess valuable pharmacological properties. The purified Type VI collagen in native state configuration exhibits only limited immunogenicity and is useful as a resorbable filling in ocular wound voids. Autologous preparations are particularly noted. Type VI collagen/βig gel, gelsix, whether originating from purified Type VI collagen in native state configuration or from denatured Type VI collagen is useful as a precursor to cxgelsix and is placed in a wound and crosslinked in situ. Formed solid items of cxgelsix may be used as wound covers or as optic elements in eye surgery where transparent elements are required. In particular applications, a surgical fields is covered with a thin sheet of cxgelsix and surgical procedures conducted below the sheet but within the eye while being observed directly.

Thus, these compositions can be used ophthalmic surgery, including radial keratotomy, and in dermal cosmetic procedures where scar and or keloid formation is of concern. In such instances the property of fibrosis limited wound healing enabled by cxgelsix offers specific advantage. In ophthalmic applications, wound healing while maintaining tissue transparency is particularly noted. Administration is contemplated to include chronic, acute or intermittent regimens.

In addition, the compositions can be used in in vitro methodologies, including as a covering for growing replacement cellular tissues such as "artificial" skin or corneas and the like. In some embodiments, tissues, cells or material treated in vitro will, thereafter, be reintroduced into a subject (which need not be the source of origin of the tissue, cells or material). Compounds of the present invention are also employed in admixture with carriers, germicides, fungicides, or soaps, etc., for use as antiseptic solutions and the like, particularly in conjunction with hospital housekeeping procedures, e.g., to combat nocosomial infections such as those arising after surgical ophthalmic or dermal insults. They are also useful as temporary or permanent prosthetic devices, such as lenses.

The compositions of this invention are generally administered to animals, including but not limited to humans.

The pharmacologically active compositions of this invention can be processed in accordance with conventional methods of Galenic pharmacy to produce medicinal agents for administration to subjects, e.g., mammals including humans.

The compositions of this invention can be employed in admixture or impregnated with conventional and or topical agents which do not deleteriously react with the active compositions. Suitable pharmaceutically acceptable carriers include but are not limited to water, and salt solutions. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins, antifungals or antibiotics.

In some embodiments of the present invention, dosage forms include instructions for the use of such compositions.

Particularly suitable are injectable, sterile solutions of gelsix, applied into a wound or traumatized area. Ampules are convenient unit dosages.

Sustained or directed release compositions contained within gelsix and cxgelsix can be formulated wherein the active component is protected with differentially degradable gel. It is also possible to freeze-dry the new compositions and use the lyophilizates obtained, for example, for the preparation of products for injection and crosslinking in situ.

For topical application, there are employed as nonsprayable forms, viscous; to semi-solid or solid forms comprising a carrier compatible with topical application and having a dynamic viscosity preferably greater than water. Suitable formulations include but are not limited to solutions, and suspensions, which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with the gel carrier material, is packaged in a squeeze bottle or in admixture with a pressurized volatile, normally gaseous propellant, e.g., a Freon.

It will be appreciated that the actual preferred amounts of compositions in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

The forgoing is merely exemplary of the invention which will be limited only by the claims. Other methods and uses of this invention will be immediately understood and do not depart from the spirit of this invention.

We claim:

1. Purified Type VI collagen/βig gel.

2. The gel of claim 1 wherein the gel is prepared from Type VI collagen/βig comprising Type VI collagen in native state configuration.

3. The gel of claim 1 wherein the gel is prepared from denatured Type VI collagen/βig.

4. A method of preparing Type VI collagen/βig gel from Type VI collagen associated with βig comprising the steps of (a) preparing a solution of purified Type VI collagen and βig;

(b) centrifuging said solution on a centrifugation concentrator filter until a meniscus of Type VI collagen/βig gel is formed on said filter.

5. Type VI collagen/βig crosslinked gel ("cxgelsix").

6. A method of preparing cxgelsix gel by the step of exposing gelsix to a crosslinking effective amount of a crosslinking agent.

7. The method of claim 6 wherein said gelsix comprises native state Type VI collagen/βig.

8. The method of claim 6 wherein said gelsix comprises denatured Type VI collagen.

9. The method of claim 6 wherein the crosslinking agent is disuccinimidyl glutarate polyethyleneglycol.

10. The method of claim 9 wherein the crosslinking effective amount is at least about 10:1 crosslinking agent to gelsix (w/w).

11. The cxgelsix product of the process of claim 6.

12. A method of potentiating fibrosis limited tissue regeneration by applying cxgelsix to a site of tissue regeneration.

13. The method of claim 12 wherein the site of tissue regeneration is an incised wound, said method comprising the step of applying said cxgelsix as a filling for said wound.

14. The method of claim 13 further comprising the steps of (a) applying cxgelsix as gelsix placed in said wound and thereafter (b) contacting said gelsix with a crosslinking agent, and (c) crosslinking gelsix into cxgelsix in situ.

15. Cxgelsix in the form of an intrastromal lens.

16. A fibrosis limiting wound healing kit comprising (a) an applicator containing gelsix (b) an aliquot of excess (relative to gelsix) crosslinking agent, and (c) instructional literature on the in situ intra-wound creation of cxgelsix.

* * * * *